United States Patent
Lim et al.

(10) Patent No.: US 12,121,618 B2
(45) Date of Patent: *Oct. 22, 2024

(54) TRANSDERMAL DRUG DELIVERY PATCH AND MANUFACTURING METHOD THEREOF

(71) Applicants: POSTECH ACADEMY-INDUSTRY FOUNDATION, Pohang-si (KR); SHILLA INDUSTRIAL CO., LTD., Gyeongsan-si (KR)

(72) Inventors: Geunbae Lim, Pohang-si (KR); Jungho Lee, Siheung-si (KR); Byoungsun Choi, Daegu (KR); Hyeonsu Woo, Pohang-si (KR)

(73) Assignees: Postech Academy-Industry Foundation, Pohang-si (KR); Shilla Industrial Co., Ltd., Gyeongsan-si (KR)

( * ) Notice: Subject to any disclaimer, the term of this patent is extended or adjusted under 35 U.S.C. 154(b) by 887 days.

This patent is subject to a terminal disclaimer.

(21) Appl. No.: 17/055,640

(22) PCT Filed: May 18, 2018

(86) PCT No.: PCT/KR2018/005739
§ 371 (c)(1),
(2) Date: Nov. 16, 2020

(87) PCT Pub. No.: WO2019/221319
PCT Pub. Date: Nov. 21, 2019

(65) Prior Publication Data
US 2021/0244681 A1 Aug. 12, 2021

(51) Int. Cl.
| | | |
|---|---|---|
| A61K 9/70 | (2006.01) | |
| A61K 9/00 | (2006.01) | |
| A61M 37/00 | (2006.01) | |
| B29C 33/38 | (2006.01) | |
| B29C 35/08 | (2006.01) | |
| B29C 41/50 | (2006.01) | |
| B29L 31/00 | (2006.01) | |

(52) U.S. Cl.
CPC .......... *A61K 9/7092* (2013.01); *A61K 9/0021* (2013.01); *A61M 37/0015* (2013.01); *B29C 33/3857* (2013.01); *B29C 35/0805* (2013.01); *B29C 41/50* (2013.01); *A61M 2037/0046* (2013.01); *A61M 2037/0053* (2013.01); *B29L 2031/7544* (2013.01)

(58) Field of Classification Search
CPC .... A61K 9/7092; A61K 9/0021; A61K 9/703; A61M 37/0015; A61M 2037/0046; A61M 2037/0053; A61M 2037/0023; B29C 41/50; B29C 39/26; B29C 39/24; B29C 41/12; B29C 41/36; B29C 33/3814; B29C 33/42; B29C 39/026; B29C 39/42; B29C 41/20; B29C 41/38; B29C 2035/0827; B29K 2105/0035; B29K 2995/006; B29K 2883/00; B29L 2031/756
See application file for complete search history.

(56) References Cited

U.S. PATENT DOCUMENTS

| | | | |
|---|---|---|---|
| 6,652,478 | B1 | 11/2003 | Gartstein et al. |
| 2002/0138049 | A1* | 9/2002 | Allen ............ A61N 1/303 264/219 |
| 2013/0338632 | A1* | 12/2013 | Kaplan ............ A61P 43/00 604/173 |
| 2018/0064920 | A1 | 3/2018 | Desimone et al. |
| 2021/0228854 | A1* | 7/2021 | Lim ............ A61K 9/0021 |

FOREIGN PATENT DOCUMENTS

| | | |
|---|---|---|
| CN | 1975569 | 6/2007 |
| CN | 101687090 | 3/2010 |
| CN | 104780968 | 7/2015 |
| CN | 106061546 | 10/2016 |
| CN | 107405301 | 11/2017 |
| EP | 2921203 | 9/2015 |
| JP | 2004-310077 | 11/2004 |
| JP | 2007-148213 | 6/2007 |
| JP | 2008-125864 | 6/2008 |
| JP | 2011-072695 | 4/2011 |
| JP | 2011-78654 | 4/2011 |
| JP | 4965053 | 7/2012 |
| JP | 2016-158930 | 9/2016 |
| JP | 2017-144307 | 8/2017 |
| KR | 10-1692266 | 1/2017 |
| KR | 10-1728526 | 4/2017 |
| KR | 10-1746747 | 6/2017 |
| KR | 10-2018-0031321 | 3/2018 |
| KR | 10-2018-0046829 | 5/2018 |
| WO | 2008-008557 | 1/2008 |
| WO | 2014-077244 | 5/2014 |

OTHER PUBLICATIONS

KIPO, International Search Report & Written Opinion of the International Searching Authority of Application No. PCT/KR2018/005739 dated May 9, 2019.
EPO, Search Report of EP 18918953.3 dated Jan. 7, 2022.
SIPO, Search Report of CN 201880095719.4 dated Feb. 23, 2022.

* cited by examiner

*Primary Examiner* — Aradhana Sasan
(74) *Attorney, Agent, or Firm* — LEX IP MEISTER, PLLC

(57) ABSTRACT

A transdermal drug delivery patch includes a flexible base layer, and a plurality of microneedles disposed at one surface of the base layer and including a biodegradable polymer and a drug. Each of a plurality of microneedles is formed as a star-shaped pyramid including a plurality of protrusions extending in a radial direction, and a concave shape is formed between two protrusions adjacent along a circumferential direction among a plurality of protrusions.

10 Claims, 13 Drawing Sheets

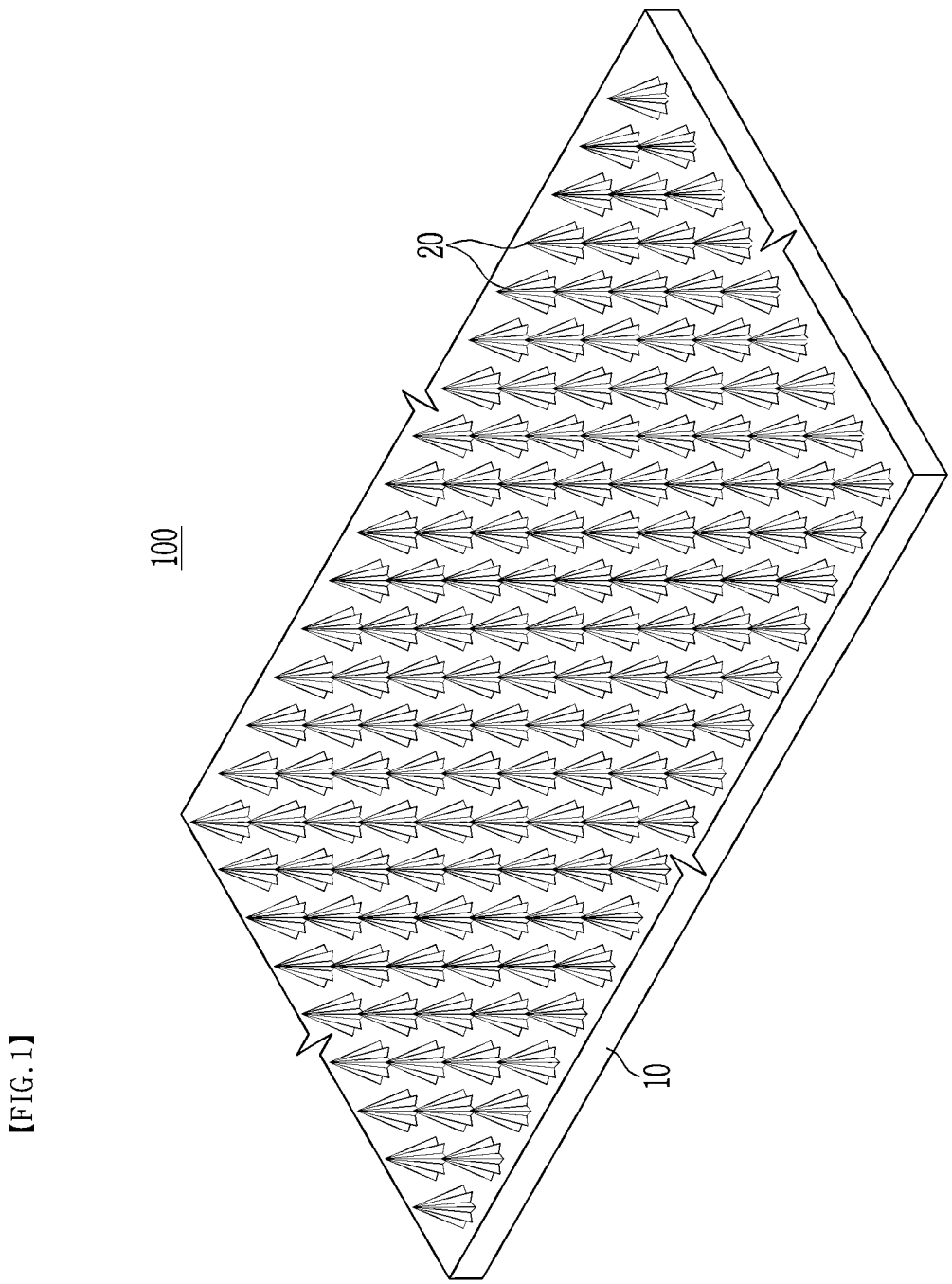
[FIG. 1]

[FIG.2]
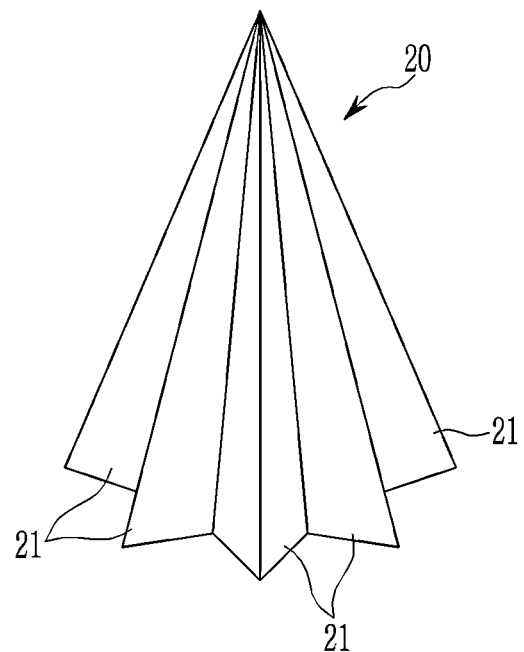
[FIG.3]
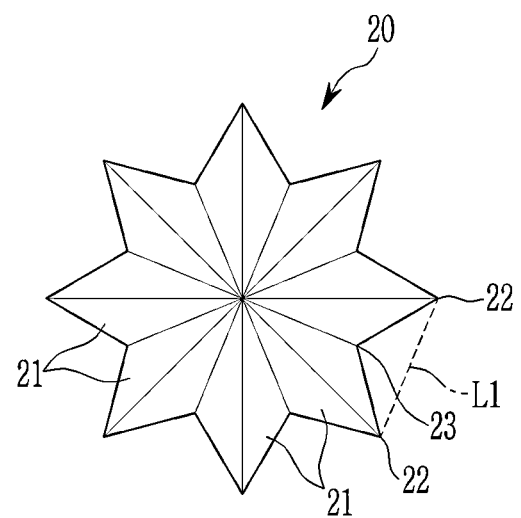

[FIG. 4]
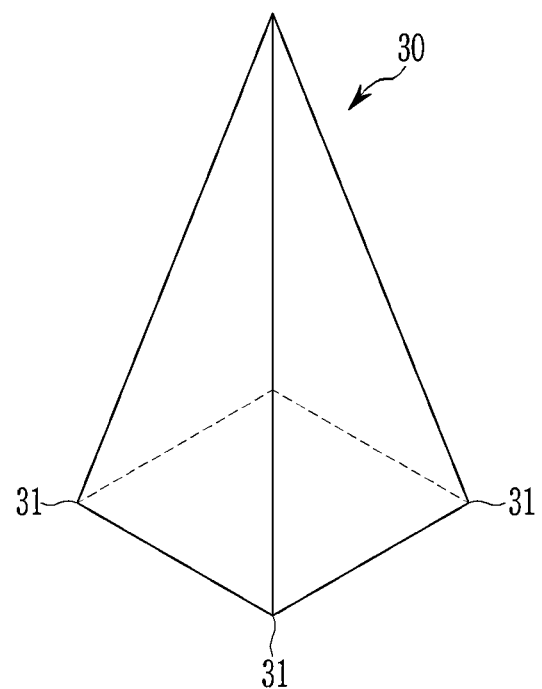
[FIG. 5]
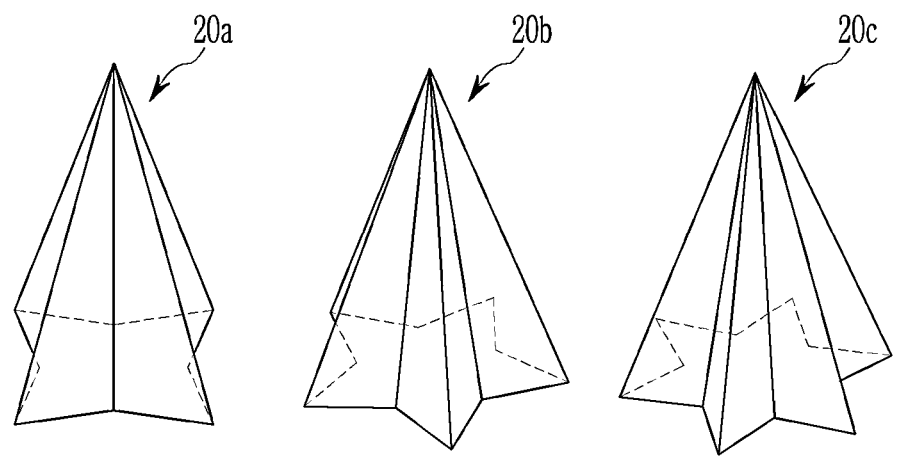

[FIG.6]
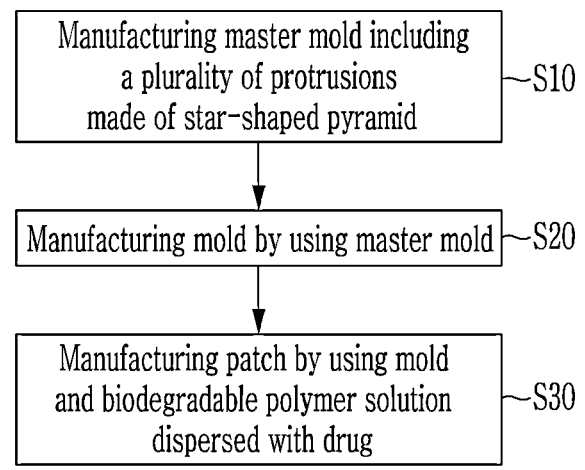

[FIG. 7A]
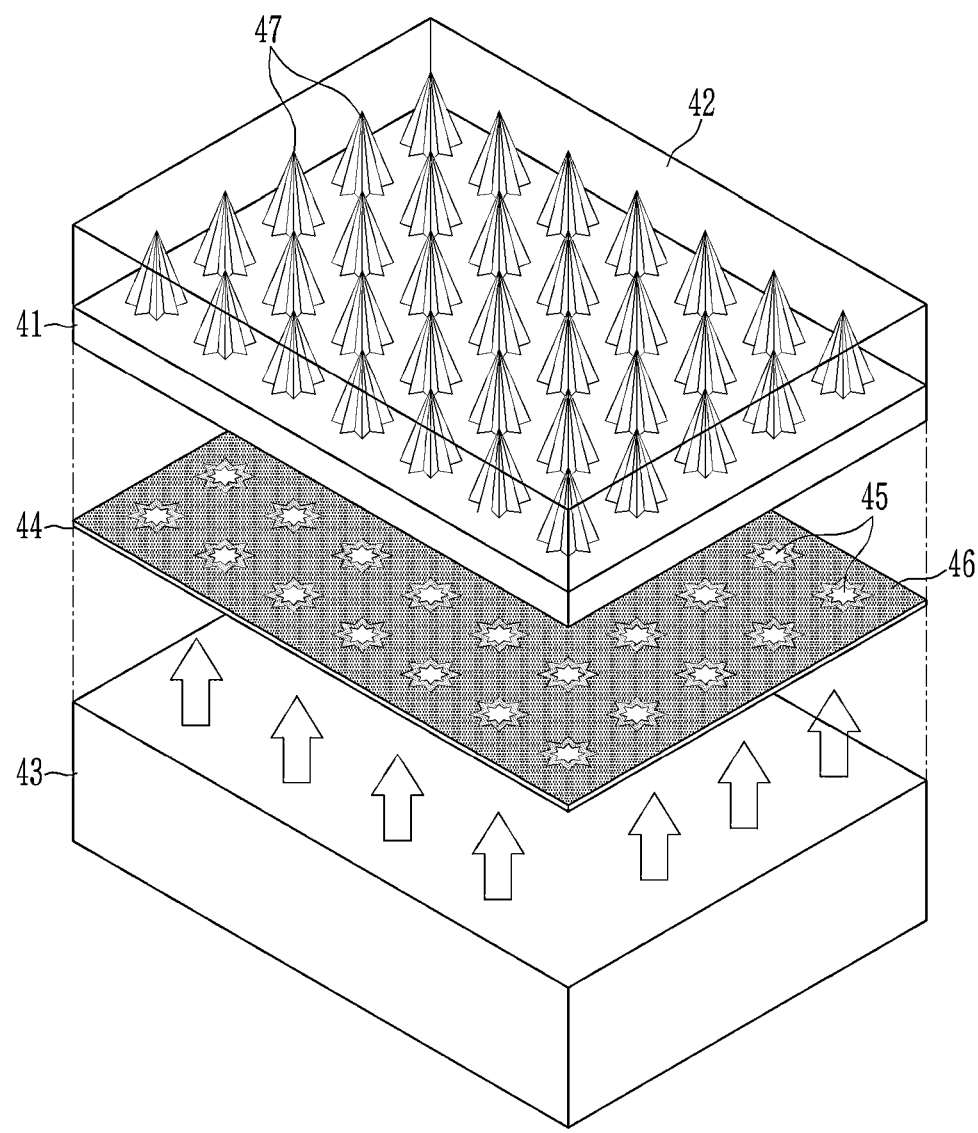

[FIG. 7B]
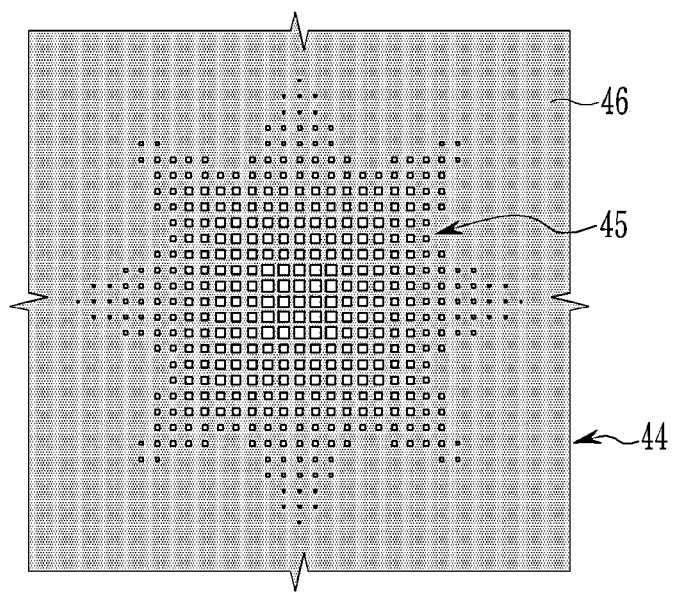
[FIG. 7C]
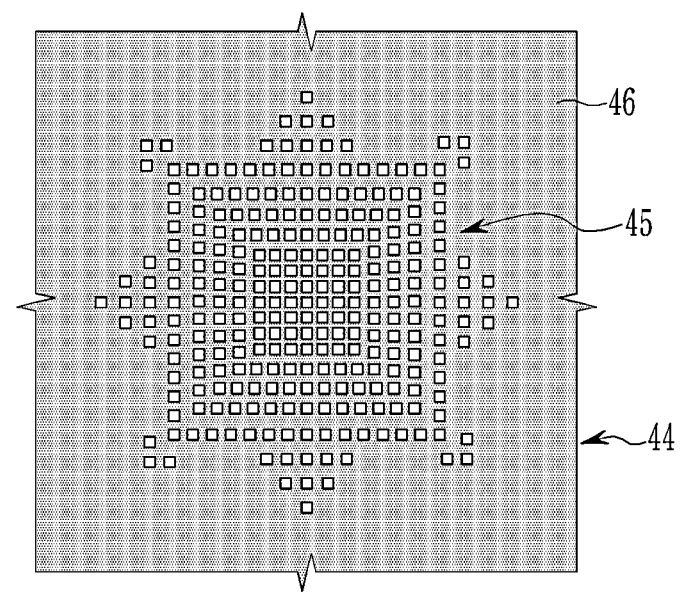

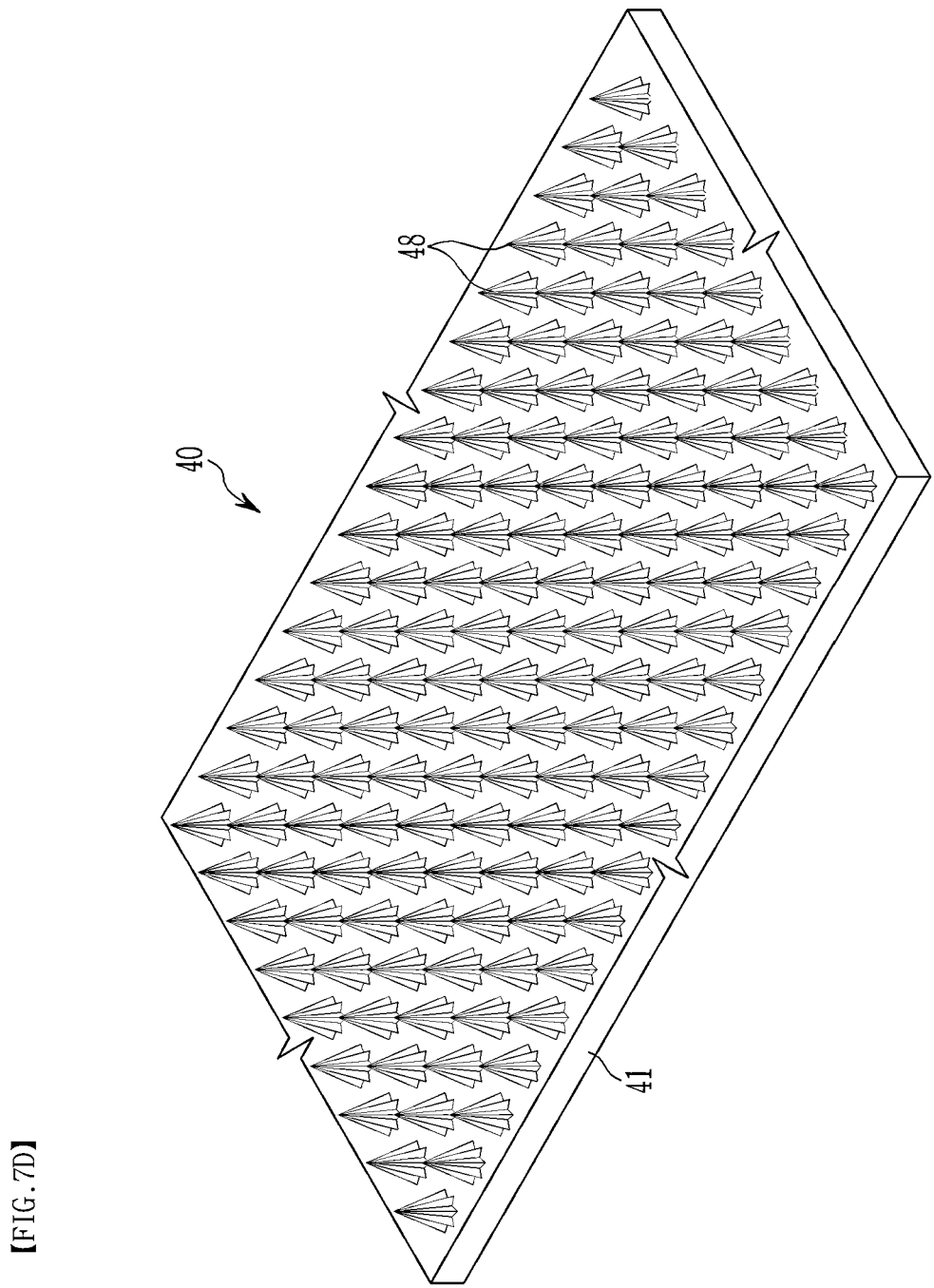
[FIG. 7D]

【FIG.8】
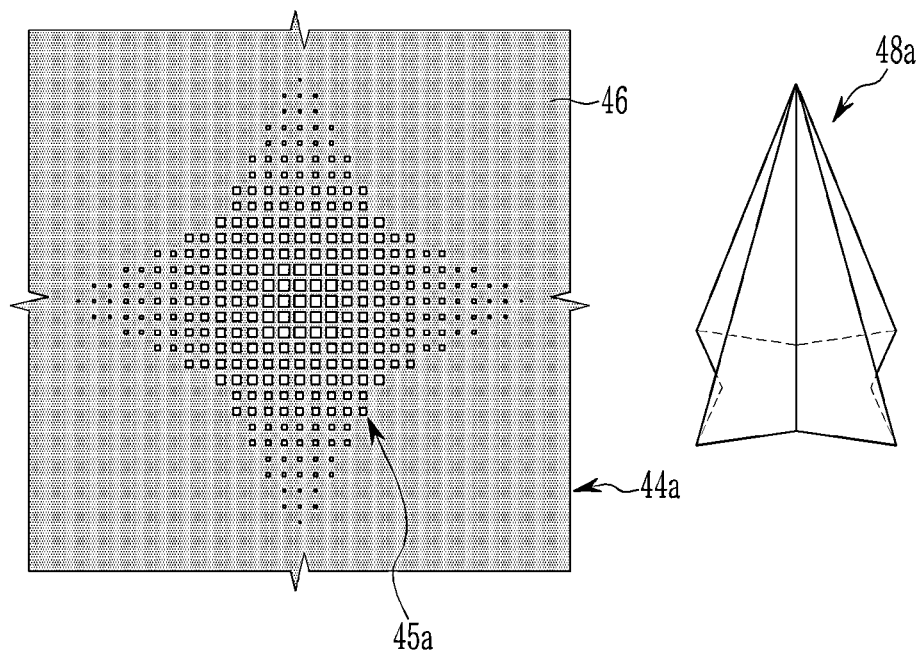
【FIG.9】
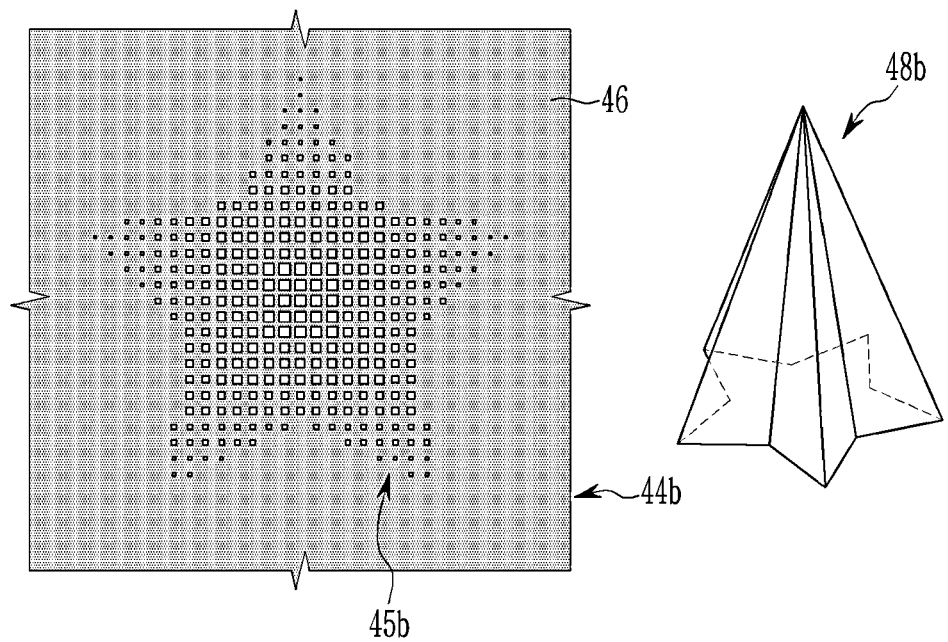

[FIG. 10]
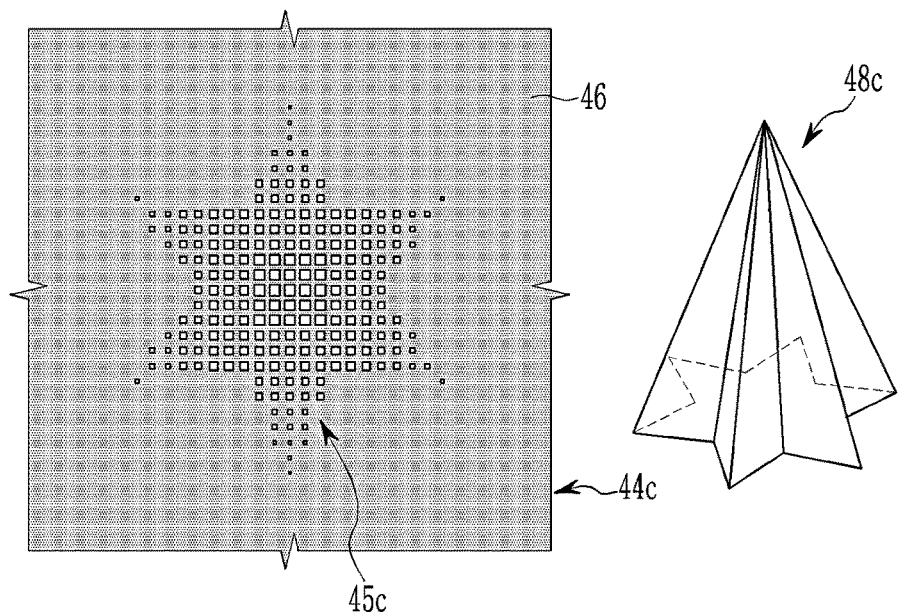
[FIG. 11A]
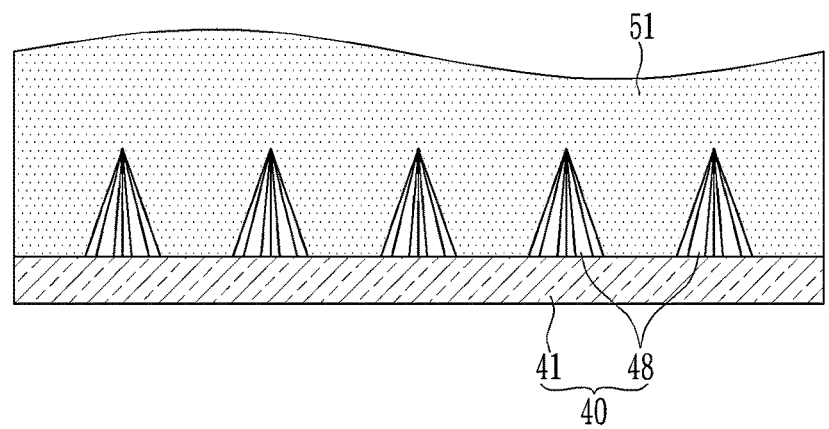

[FIG. 11B]
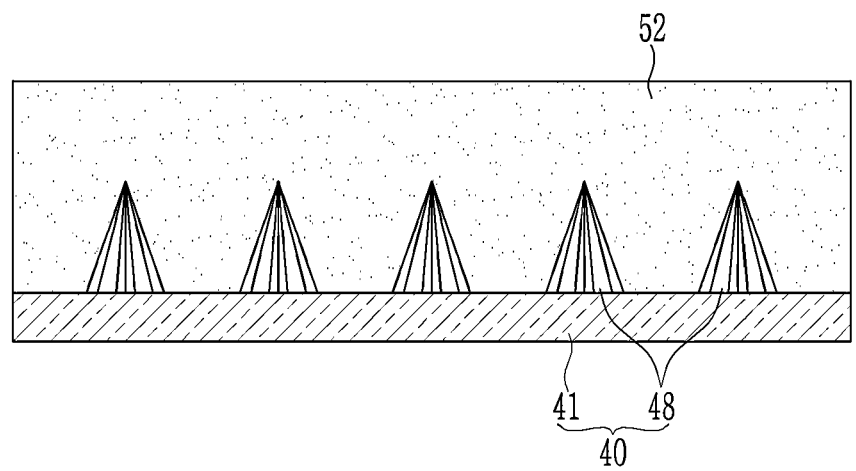
[FIG. 11C]
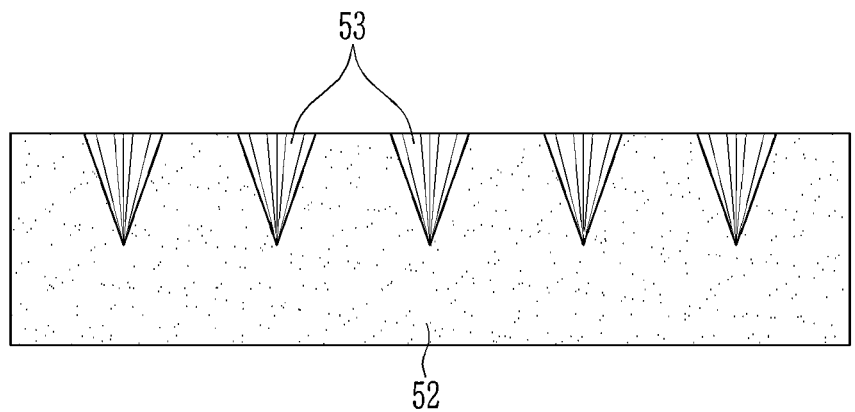

[FIG. 12A]
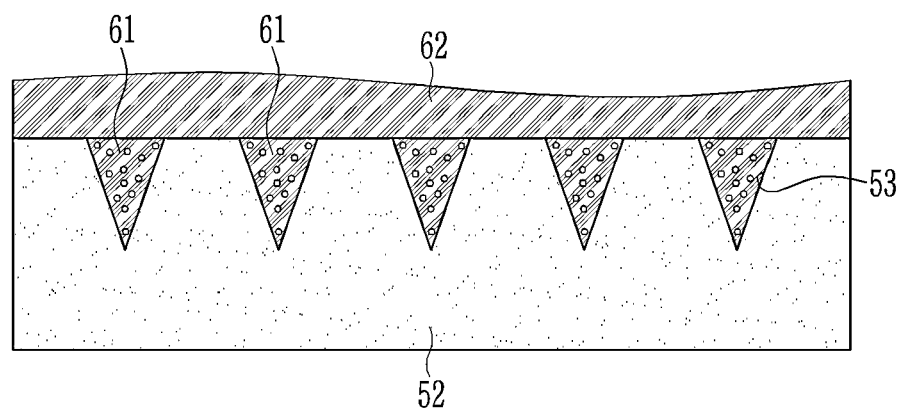
[FIG. 12B]
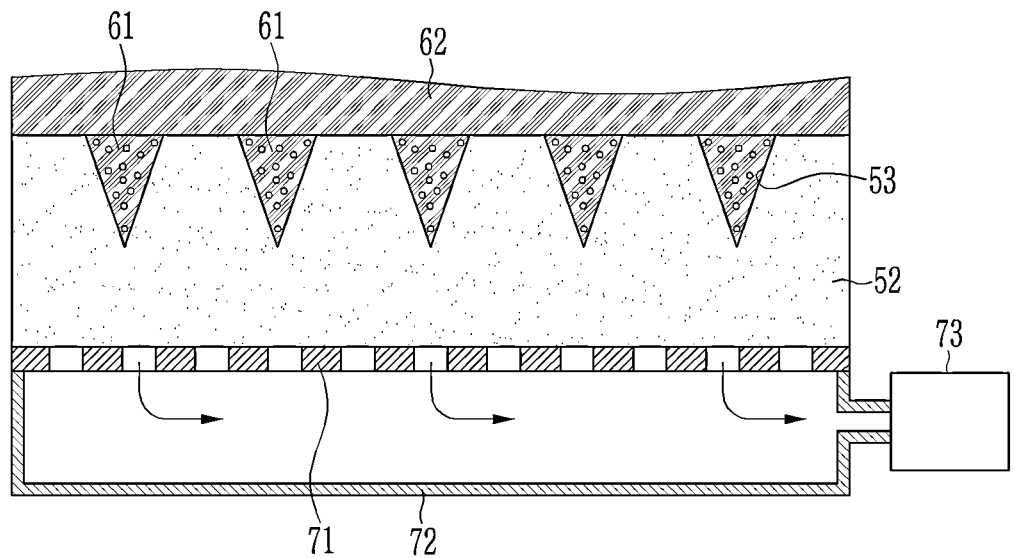

[FIG. 12C]
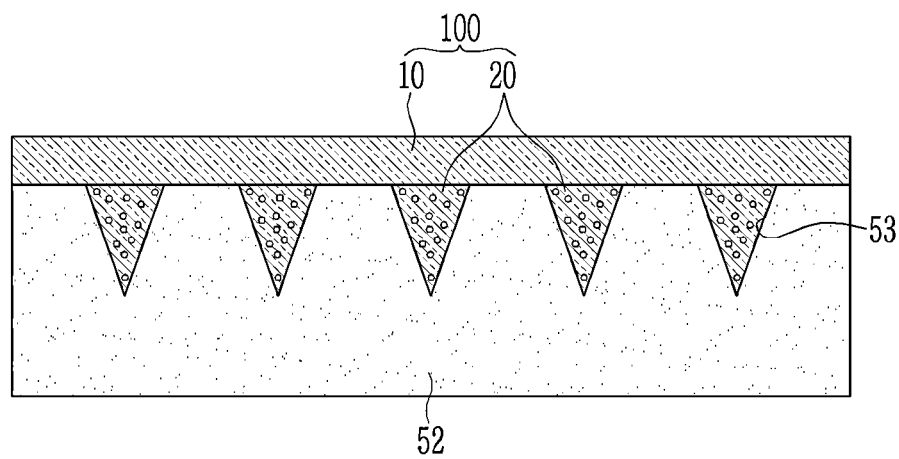

[FIG. 12D]
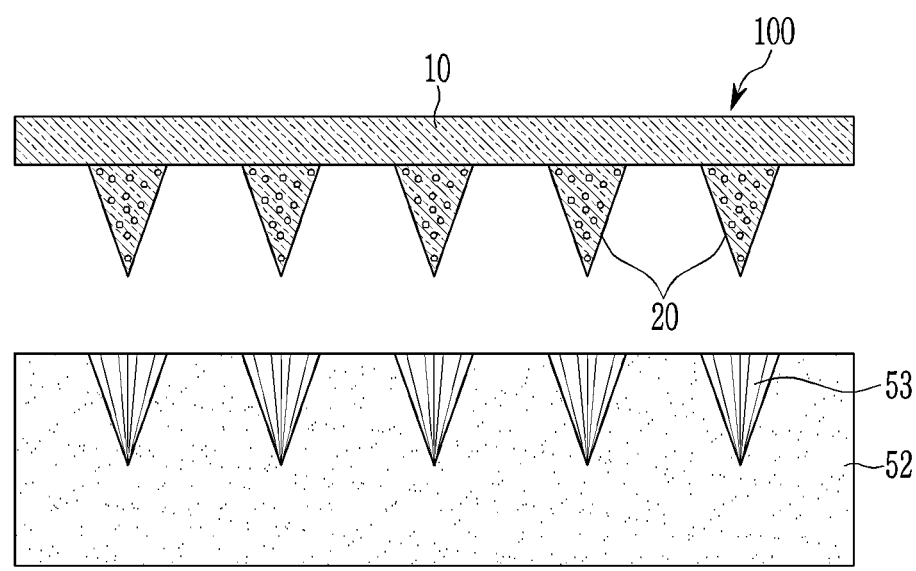

TRANSDERMAL DRUG DELIVERY PATCH AND MANUFACTURING METHOD THEREOF

TECHNICAL FIELD

The present invention relates to a transdermal drug delivery patch. More particularly, the present invention relates to a transdermal drug delivery patch and a manufacturing method thereof for a surface area expansion of a microneedle.

BACKGROUND ART

A transdermal drug delivery patch (hereinafter, referred to as 'a patch' for convenience) includes a microneedle made of a biodegradable polymer loaded with a drug.

The microneedle penetrates the stratum corneum of skin, penetrates into the epidermis or dermis of the skin, and stay in the skin for several minutes to several hours to allow a drug to decompose by body fluids and to be absorbed into the body. Unlike a conventional syringe, these patches cause little bleeding and pain in the drug delivery process.

When the surface area of the microneedle is wider than the volume, the area in contact with the body fluid of the skin is enlarged, and the biodegradable polymer is rapidly dissolved, thereby increasing the absorption efficiency of the drug. However, for convenience of manufacturing, the conventional patch mainly has microneedles that have a simple shape such as a cone or a quadrangular pyramid and have a small surface area compared to the volume, so there is a limitation in enhancing the absorption efficiency of the drug.

DISCLOSURE

Technical Problem

The present invention is to provide a transdermal drug delivery patch and a manufacturing method thereof that may increase the absorption efficiency of drugs by providing a microneedle with a large surface area compared to the volume while maintaining a high aspect ratio.

Technical Solution

A transdermal drug delivery patch according to an exemplary embodiment of the present invention includes a flexible base layer, and a plurality of microneedles disposed at one surface of the base layer and including a biodegradable polymer and a drug. Each of a plurality of microneedles is formed as a star-shaped pyramid including a plurality of protrusions extending in a radial direction, and a concave shape is formed between two protrusions adjacent along a circumferential direction among a plurality of protrusions.

In each of a plurality of microneedles, each protruded length of a plurality of protrusions according to the radial direction may be the same, and a distance between two protrusions adjacent along the circumferential direction of a plurality of protrusions may be the same. The plurality of protrusions may be 3 or more to 20 or less.

A manufacturing method of a transdermal drug delivery patch according to an exemplary embodiment of the present invention includes: (1) manufacturing a master mold including a transparent plate and a plurality of protruded portions disposed at one surface of the transparent plate and made as a star-shaped pyramid including a plurality of protrusions extending in a radial direction; (2) manufacturing a mold including a plurality of recess portions having a shape corresponding to a plurality of protruded portions by using the master mold; and (3) manufacturing a transdermal drug delivery patch including a base layer and a plurality of microneedles disposed at one surface of the base layer and having a shape corresponding to a plurality of recess portions by using the mold, a drug, and a biodegradable polymer solution.

The manufacturing of the master mold may include: forming a photo-curable polymer layer on a transparent plate; disposing a grayscale mask between a light source and the transparent plate; and irradiating light to the photo-curable polymer layer through the grayscale mask to cure a part of the photo-curable polymer layer.

The grayscale mask may include a star-shaped light transmission part including a plurality of protrusions extending in a radial direction and a light blocking part other than the light transmission part. A light transmission rate of the light transmission part may decrease further away from the center of the light transmission part.

The light transmission part may be composed of a plurality of dots, and the plurality of dots may have a smaller size further away from the center of the light transmission part. On the other hand, the light transmission part may be composed of a plurality of dots having the same size, and the distance between the plurality of dots may increase further away from the center of the light transmission part.

The manufacturing of the mold may include coating a polymer solution on the master mold to form a polymer layer, and applying light to the polymer layer to be cured. Before curing the polymer layer, a negative pressure may be applied to the polymer layer to remove microbubbles included in the polymer layer.

The manufacturing of the transdermal drug delivery patch may include: filling a material solution in which a biodegradable polymer solution and a drug are mixed to a plurality of recess portions included in the mold; coating a biodegradable polymer solution on the mold; drying the biodegradable polymer solution and the material solution to manufacture the base layer and a plurality of microneedles; and separating the base layer and the plurality of microneedles from the mold.

Before drying the biodegradable polymer solution and the material solution, a vacuum filter and a vacuum chamber may be disposed at the rear surface of the mold, a vacuum pump connected to the vacuum chamber may be operated, and a negative pressure in a single direction may be applied to the biodegradable polymer solution and the material solution through the mold and the vacuum filter to remove microbubbles included in the biodegradable polymer solution and the material solution.

Advantageous Effects

According to the present invention, the microneedle composed as a star-shaped pyramid has an enlarged surface area by the protruded shape of the protrusions and the concave shape between the protrusions. The wider the surface area, the faster the absorption speed of the body fluids as the microneedle penetrating into the epidermis or dermis of the skin is in wide contact with the body fluids. Therefore, the biodegradable polymer that constitutes the microneedle may quickly dissolve and release the drug quickly.

DESCRIPTION OF THE DRAWINGS

FIG. 1 is a perspective view of a transdermal drug delivery patch according to an exemplary embodiment of the present invention.

FIG. 2 is an enlarged perspective view of one microneedle among a transdermal drug delivery patch of FIG. 1.

FIG. 3 is a top plan view of a microneedle shown in FIG. 2.

FIG. 4 is a perspective view of a microneedle made with a quadrangular pyramid shape according to a comparative example.

FIG. 5 is a perspective view showing a microneedle according to exemplary variations that may be realized.

FIG. 6 is a process flowchart showing a manufacturing method of a patch according to an exemplary embodiment of the present invention.

FIG. 7A to FIG. 7D are views showing a manufacturing process of a master mold of a first step shown in FIG. 6.

FIG. 8 to FIG. 10 are views showing a light transmission part shown in FIG. 7A and a protrusion shown in FIG. 7D according to an exemplary variation.

FIG. 11A to FIG. 11C are views showing a manufacturing process of a mold of a second step shown in FIG. 6.

FIG. 12A to FIG. 12D are views showing a manufacturing process of a patch of a third step shown in FIG. 6.

MODE FOR INVENTION

The present invention will be described more fully hereinafter with reference to the accompanying drawings, in which exemplary embodiments of the invention are shown. As those skilled in the art would realize, the described embodiments may be modified in various different ways, all without departing from the scope of the present invention.

FIG. 1 is a perspective view of a transdermal drug delivery patch according to an exemplary embodiment of the present invention, FIG. 2 is an enlarged perspective view of one microneedle among a transdermal drug delivery patch of FIG. 1, and FIG. 3 is a top plan view of a microneedle shown in FIG. 2.

Referring to FIG. 1 to FIG. 3, a patch 100 according to the present exemplary embodiment consists of a base layer 10 and a plurality of microneedles 20 disposed at one surface of the base layer 10. The base layer 10 is a flexible supporter that supports a plurality of microneedles 20, and may be composed of a biodegradable polymer film having a predetermined thickness that is easily bent to be suitable to the curvature of the skin.

A plurality of microneedles 20 may have the same size and the same shape and may be aligned side by side with a distance from each other at one surface of the base layer 20

The microneedle 20 is made of a biodegradable polymer dispersed with the drug in a powder or liquid form, and penetrates a stratum corneum of the skin and penetrates into an epidermis or dermis of the skin.

The biodegradable polymer constituting the patch 100 may include at least one of hyaluronic acid, carboxymethyl cellulose, and polyvinyl alcohol, but is not limited to this example. The microneedle 20 is decomposed by a body fluid while staying in the epidermis or dermis of the skin for several minutes to several hours to absorb the drug into the body.

In the patch 100 of the present exemplary embodiment, the microneedle 20 is made as a star-shaped pyramid including a plurality of protrusions 21 extending in the radial direction. In the entire specification, 'the radial direction' refers to the direction extending from the center of the microneedle 20 in all directions when viewing the microneedle 20 from the top (i.e., on the plane of the microneedle 20).

In FIG. 2 and FIG. 3, the microneedle 20 made of an octagonal star-shaped pyramid is shown as an example.

The plurality of protrusions 21 extend parallel to the radial direction from the center of the microneedle 10, and the size of the protrusion 12 gradually decreases as the distance from the base layer 10 increases. Further, among a plurality of protrusions 21, a concave shape is formed between two protrusions 21 adjacent along the circumferential direction. In the entire specification, 'the circumferential direction' means the direction surrounding the microneedle 20 once.

The fact that a plurality of protrusions 21 extend in the radial direction and two protrusions 21 adjacent along the circumferential direction form the concave shape is an important shape characteristic that is distinguished from a microneedle having a polygonal pyramid shape such as a quadrangular pyramid.

FIG. 4 is a perspective view of a microneedle made with a quadrangular pyramid shape according to a comparative example. Referring to FIG. 4, the microneedle 30 with the quadrangular pyramid shape has four corners 31 when viewed from above, and a straight line is formed between two corners 31 adjacent to each other among four corners 31.

Again referring to FIG. 2 and FIG. 3, in the patch 100 according to the present exemplary embodiment, when assuming an imaginary line L1 that connects two protrusions 21 adjacent along the circumferential direction by a shortest distance among a plurality of protrusions 21 included in the microneedle 20, the space between the two protrusions 21 is disposed more inward toward the center of the microneedle 10 than this imaginary line L1.

Specifically, each of a plurality of protrusions 21 is composed of a pointed end portion 22 and a root portion 23 connected to the neighboring protrusion 21, and the root portion 23 is disposed more inward toward the center of the microneedle 20 than the imaginary line L1 connecting two end portions 22 adjacent to each other along the circumferential direction with the shortest distance.

Each protruded length of a plurality of protrusions 21 according to the radial direction may be the same, and the distance between two end portions 22 adjacent to each other in the circumferential direction among the plurality of protrusions 21 may be the same. That is, the microneedles 20 may achieve rotational symmetry. The microneedles 20, which form a rotationally symmetrical shape, may be in uniformly contact with a body fluid on the entire surface to increase the decomposition efficiency of the biodegradable polymer.

As such, the microneedle 20 composed of the star-shaped pyramid has a surface area that is enlarged by the concave shape between the protruded shape of protrusions 21 and the protrusions 21. That is, the microneedle 20 composed of the star-shaped pyramid has the enlarged surface area compared to that of the microneedle of a conical and quadrangular pyramid shape having the same width and height.

The wider the surface area, the faster the absorption speed of the body fluid as the microneedle 20 that has penetrated into the epidermis or dermis of the skin is in wide contact with the body fluid. Therefore, the biodegradable polymer constituting the microneedle 20 may quickly dissolve and release the drug.

The number of protrusions 21 constituting the microneedle 20 in the patch 100 of the present exemplary embodiment is not limited to eight, and may be variously changed. Specifically, the number of the protrusions 21 constituting the microneedle 20 is 3 or more, and preferably may belong to a range of 3 to 20.

When the number of protrusions 21 is 3 or more, the microneedle 20 may implement a star-shaped pyramid. If the number of protrusions 21 exceeds 20, the manufacturing process of the patch 100 is complicated, and the effect of expanding the surface area is less compared to that of a cone.

FIG. 5 is a perspective view showing a microneedle according to exemplary variations that may be realized. In FIG. 5, a microneedle 20a with the quadrangle star shape of a pyramid for each square, a microneedle 20b in the pentagon star shape of a pyramid, and a microneedle 20c in the hexagonal shape of a pyramid are shown as examples.

Again referring to FIG. 1 to FIG. 3, the patch 100 of the present exemplary embodiment may effectively enlarge the surface area of the microneedle 20 while maintaining the high aspect ratio of the microneedle 20, resulting in increasing the absorption efficiency of the drug and the drug may be absorbed into the body in a shorter time.

Next, a manufacturing method of the patch according to the present exemplary embodiment is described. FIG. 6 is a process flowchart showing a manufacturing method of a patch according to an exemplary embodiment of the present invention.

Referring to FIG. 6, the manufacturing method of the patch includes a first step (S10) of manufacturing a master mold including a plurality of protruded portions made of a star-shaped pyramid, a second step (S20) of manufacturing a mold by using the master mold, and a third step (S30) of manufacturing a patch including a base layer and a plurality of microneedles by using the mold.

FIG. 7A to FIG. 7D are views showing a manufacturing process of a master mold of a first step shown in FIG. 6.

Referring to FIG. 7A to FIG. 7C, a photo-curable polymer layer 42 is disposed on a transparent plate 41 such as a glass plate, and a grayscale mask 44 is disposed between a light source 43 and the transparent plate 41. The light source 43 may be composed of an ultraviolet ray collimated light exposer, and the photo-curable polymer layer 42 may include an ultraviolet ray curable polymer.

The grayscale mask 44 is an exposure mask including a plurality of regions having different light transmission rates. In the present exemplary embodiment, the grayscale mask 44 includes a star-shaped light transmission part 45 including a plurality of protrusions extending in a radial direction and a light blocking part 46 other than the light transmission part 45.

The light blocking part 46 may be a metal layer that blocks ultraviolet rays, and the light transmission part 45 may be an open area without a metal layer. In FIG. 7A to FIG. 7C, octagonal star-shaped light transmission parts 45 are illustrated as examples.

In the grayscale mask 44, the light transmission part 45 has a light transmission rate that becomes smaller further away from the center. To this end, the light transmission part 45 may be composed of a plurality of dots, and a plurality of dots may have a smaller size further away from the center of the light transmission part 45 (referring to FIG. 7B). On the other hand, the light transmission part 45 may be composed of a plurality of dots having the same size, and the distance between the dots may be increased further away from the center of the light transmission part 45 (referring to FIG. 7C).

When the light source 43 is operated and light is irradiated to the photo-curable polymer layer 42 through the grayscale mask 44, the photo-curable polymer layer 42 in a position corresponding to the light transmission part 45 is cured by light. At this time, the shape of the cured structure 47 corresponds to the planar shape of the light transmission part 45, and the height of the cured structure 47 is proportional to the light intensity of the light source 43 and the light transmission rate of the light transmission part 45.

As shown in FIG. 7B and FIG. 7C, when the grayscale mask 44 has the octagonal star-shaped light transmission part 45, the cured structure 47 is formed in the form of an octagonal star-shaped pyramid whose height decreases further away from the center.

The photo-curable polymer layer 42 on the transparent plate 41 is divided into a cured part and an uncured part, and the uncured part is removed by developing. Then, as shown in FIG. 7D, the master mold 40 consisting of the transparent plate 41 and a plurality of protruded portions 48 arranged on one surface of the transparent plate 41 is completed. A plurality of protruded portions 48 are made as octagonal star-shaped pyramids.

FIG. 8 to FIG. 10 are views showing light transmission parts shown in FIG. 7A and protrusions shown in FIG. 7D according to exemplary variations.

Referring to FIG. 8, a light transmission part 45a includes four protrusions extending in a radial direction and has a light transmission rate that decreases further away from the center. A protruded portion 48a of the master mold manufactured using this grayscale mask 44a is made as a square star-shaped pyramid.

Referring to FIG. 9, a light transmission part 45b includes five protrusions extending in a radial direction and has a light transmission rate that decreases further away from the center. A protruded portion 48b of the master mold manufactured using this grayscale mask 44b is made as a pentagonal star-shaped pyramid.

Referring to FIG. 10, a light transmission part 45c includes six protrusions extending in a radial direction and has a light transmission rate that decreases further away from the center. A protruded portion 48c of the master mold manufactured using this grayscale mask 44c is made of a hexagonal star-shaped pyramid.

In FIG. 8 to FIG. 10, the light transmission parts 45a, 45b, and 45c composed of a plurality of dots having a smaller size further away from the center are illustrated as examples, but the light transmission parts 45a, 45b, and 45c may be composed of a plurality of dots that all have the same size with increasing distances between them further away from the center as shown in FIG. 7C.

By changing the shape of the light transmission part 45 in this way, the star-shaped pyramid protruded portion 48 having the number of protrusions in the range of 3 or more, preferably 3 to 20, may be manufactured.

FIG. 11A to FIG. 11C are views showing a manufacturing process of a mold of a second step shown in FIG. 6.

Referring to FIG. 11A to FIG. 11C, a polymer solution is coated on a master mold 40 to form a polymer layer 51. The polymer layer 51 may include a thermosetting resin. The polymer layer 51 may include, for example, polydimethylsiloxane, but is not limited to this example.

At this time, the microbubbles may be positioned around the surface of the polymer layer 51 in contact with the master mold 40, and the microbubbles may be removed by applying a negative pressure to the polymer layer 51 by using a vacuum device (although not shown).

Subsequently, heat is applied to the polymer layer 51 to be cured, and the master mold 40 is separated from the cured mold 52 to complete the mold 52 having a plurality of recess portions 53. The mold 52 may have a plate structure with a predetermined thickness, and a plurality of recess portions 53 having a shape corresponding to the protruded portion 48 of the master mold 40 are disposed on one surface of the mold 52.

FIG. 12A to FIG. 12D are views showing a manufacturing process of a patch of a third step shown in FIG. 6.

Referring to FIG. 12A, a material solution 61 is prepared by dispersing the drug of a powder or liquid form in a biodegradable polymer solution, and the material solution 61 is coated to the surface of the mold 52 where the plurality of recess portions 53 are disposed. The coated material solution 61 flows into the plurality of recess portions 53 and fills the plurality of recess portions 53.

Subsequently, a biodegradable polymer solution 62 is coated on the mold 52 again to cover the surface of the mold 52 and the material solution 61 filled in the plurality of recess portions 53. At this time, the microbubbles may exist on the surface or inside of the material solution 61 and the biodegradable polymer solution 62.

Referring to FIG. 12B, a vacuum filter 71 and a vacuum chamber 72 are disposed at the rear surface of the mold 52. The vacuum filter 71 is composed of a porous plate in which a plurality of holes are formed, and the vacuum chamber 72 includes an internal space connected to the vacuum pump 73. The mold 52 is an ultra-micropore structure that is hardened but contains numerous micropores inside.

When a vacuum pump 73 is started, a negative pressure is applied to the material solution 61 and the biodegradable polymer solution 62 through the vacuum filter 71 and the mold 52. The negative pressure at this time is not a pressure applied in all directions, but it is a pressure of a single direction from the material solution 61 and the biodegradable polymer solution 62 toward the mold 52.

Assuming that the negative pressure is applied in all directions, when the viscosity of the material solution 61 and the biodegradable polymer solution 62 is high, the bubbles may not escape smoothly, resulting in shape distortion. In other words, a surface film is formed on the surface exposed to the air while the air bubbles have not escaped to the outside of the surface, and the air bubbles are contained therein and hardened.

However, if the negative pressure is applied in one direction from the back side of the mold 52, the microbubbles contained in the material solution 61 and the biodegradable polymer solution 62 may be easily removed without deforming. Particularly, the microbubbles contained in the material solution 61 filled in the recess portion 53 of the mold 52 may easily escape through the mold 52 and the vacuum filter 71.

Referring to FIG. 12C and FIG. 12D, the material solution 61 filled in the plurality of recess portions 53 and the biodegradable polymer solution 62 on the surface of the mold 52 are dried and hardened into a patch 100 of a solid type, and then the patch 100 is separated from the mold 52. The patch 100 includes a base layer 10 cured with the biodegradable polymer solution 62 and a plurality of microneedles 20 cured with the material solution 61 filled in a plurality of recess portions 53.

According to the above-described method, a plurality of molds 52 may be mass-produced by manufacturing one master mold 40, and the patch 100 may be easily manufactured using a plurality of molds 52. In addition, it is possible to manufacture a plurality of microneedles 20 having excellent formation accuracy without air bubbles on the surface or inside.

A plurality of microneedles 20 included in the patch 100 are formed as the same star-shaped pyramid as the protruded portion 48 of the master mold 40, and the absorption efficiency of the drug may be increased by the enlarged surface area.

While this invention has been described in connection with what is presently considered to be practical exemplary embodiments, it is to be understood that the invention is not limited to the disclosed embodiments. On the contrary, it is intended to cover various modifications and equivalent arrangements included within the scope of the appended claims.

The invention claimed is:

1. A manufacturing method of a transdermal drug delivery patch, comprising:
   manufacturing a master mold including a transparent plate and a plurality of protruded portions disposed at one surface of the transparent plate and made as a star-shaped pyramid including a plurality of protrusions extending in a radial direction;
   manufacturing a mold including a plurality of recess portions having a shape corresponding to a plurality of protruded portions by using the master mold; and
   manufacturing a transdermal drug delivery patch including a base layer and a plurality of microneedles disposed at one surface of the base layer and having a shape corresponding to a plurality of recess portions by using the mold, a drug, and a biodegradable polymer solution,
   wherein
   the manufacturing of the master mold includes:
   forming a photo-curable polymer layer on a transparent plate;
   disposing a grayscale mask between a light source and the transparent plate; and
   irradiating light to the photo-curable polymer layer through the grayscale mask to cure a part of the photo-curable polymer layer,
   wherein
   the grayscale mask includes a star-shaped light transmission part including a plurality of protrusions extending in a radial direction and a light blocking part other than the light transmission part, and
   a light transmission rate of the light transmission part decreases further away from the center of the light transmission part.

2. The manufacturing method of the transdermal drug delivery patch of claim 1, wherein
   the light transmission part is composed of a plurality of dots, and
   the plurality of dots have a smaller size further away from the center of the light transmission part.

3. The manufacturing method of the transdermal drug delivery patch of claim 1, wherein
   the light transmission part is composed of a plurality of dots having the same size, and
   the distance between the plurality of dots increases further away from the center of the light transmission part.

4. The manufacturing method of the transdermal drug delivery patch of claim 1, wherein
   the manufacturing of the mold includes
   coating a polymer solution on the master mold to form a polymer layer, and
   applying light to the polymer layer to be cured.

5. The manufacturing method of the transdermal drug delivery patch of claim 4, wherein
   before curing the polymer layer, a negative pressure is applied to the polymer layer to remove microbubbles included in the polymer layer.

6. The manufacturing method of the transdermal drug delivery patch of claim 1, wherein
the manufacturing of the transdermal drug delivery patch includes:
filling a material solution in which a biodegradable polymer solution and a drug are mixed to a plurality of recess portions included in the mold;
coating a biodegradable polymer solution on the mold;
drying the biodegradable polymer solution and the material solution to manufacture the base layer and a plurality of microneedles; and
separating the base layer and the plurality of microneedles from the mold.

7. The manufacturing method of the transdermal drug delivery patch of claim 6, wherein
before drying the biodegradable polymer solution and the material solution,
a vacuum filter and a vacuum chamber are disposed at the rear surface of the mold, a vacuum pump connected to the vacuum chamber is operated, and
a negative pressure in a single direction is applied to the biodegradable polymer solution and the material solution through the mold and the vacuum filter to remove microbubbles included in the biodegradable polymer solution and the material solution.

8. A transdermal drug delivery patch prepared by the manufacturing method of claim 1, comprising:
a flexible base layer; and
a plurality of microneedles disposed at one surface of the base layer and including a biodegradable polymer and a drug,
wherein each of a plurality of microneedles is formed as a star-shaped pyramid including a plurality of protrusions extending in a radial direction, and
a concave shape is formed between two protrusions adjacent along a circumferential direction among a plurality of protrusions.

9. The transdermal drug delivery patch of claim 8, wherein
in each of a plurality of microneedles, each protruded length of a plurality of protrusions according to the radial direction is all the same, and a distance between two protrusions adjacent along the circumferential direction of a plurality of protrusions is the same.

10. The transdermal drug delivery patch of claim 9, wherein
the plurality of protrusions are 3 or more to 20 or less.

* * * * *